United States Patent [19]

Forster et al.

[11] 4,405,988

[45] Sep. 20, 1983

[54] PROCESS AND DEVICE FOR MONITORING THE FUNCTIONING OF A LIQUID-LIQUID EXTRACTION COLUMN

[75] Inventors: Michel Forster, Valence; Adrien Jaouen, Champigny; Alain Jorda, Massy; Pierre Rampin, Valence, all of France

[73] Assignee: Commissariat a l'Energie Atomique, Paris, France

[21] Appl. No.: 241,472

[22] Filed: Mar. 9, 1981

[30] Foreign Application Priority Data

Mar. 12, 1980 [FR] France ................................ 80 05526

[51] Int. Cl.³ .............................................. G01F 1/66
[52] U.S. Cl. .................................. 364/502; 364/509; 73/861.29
[58] Field of Search ................ 364/502, 509; 210/634; 422/105, 106, 110, 59, 68, 256; 73/53, 597, 61.1 R, 861.19–861.31

[56] References Cited

U.S. PATENT DOCUMENTS

| | | | |
|---|---|---|---|
| 3,806,449 | 4/1974 | Kaiser | 210/634 |
| 4,221,128 | 9/1980 | Lawson et al. | 73/861.29 |
| 4,232,548 | 11/1980 | Baumoel | 73/861.28 |
| 4,262,545 | 4/1981 | Lamarche et al. | 73/861.27 |
| 4,300,394 | 11/1981 | Wiley | 73/597 |
| 4,312,238 | 1/1982 | Rey | 73/861.28 |

Primary Examiner—Edward J. Wise

[57] ABSTRACT

The invention relates to a process for monitoring the functioning of a liquid-liquid extraction column in which non-mixing liquids L1 and L2 circulate in counter-current.

To this end, an ultrasonic signal is emitted at point Pn of the decanter and this ultrasonic signal is detected at Point P'n located at distance H from point Pn and the time $t_n$ taken by this signal to cover distance H is determined; the speed $v_2$ of propagation of an ultrasonic signal in the liquid medium near point Pn, preferably constituted by pure liquid L2, is also determined, as well as the speed $v_1$ of propagation of the same ultrasonic signal in the liquid medium near the point P'n, i.e. in the liquid L1, and the level h of the interphase in the decanter is determined by using the formula:

$$h = \frac{t_n - \frac{H}{v_2}}{\frac{1}{v_1} - \frac{1}{v_2}}$$

12 Claims, 1 Drawing Figure

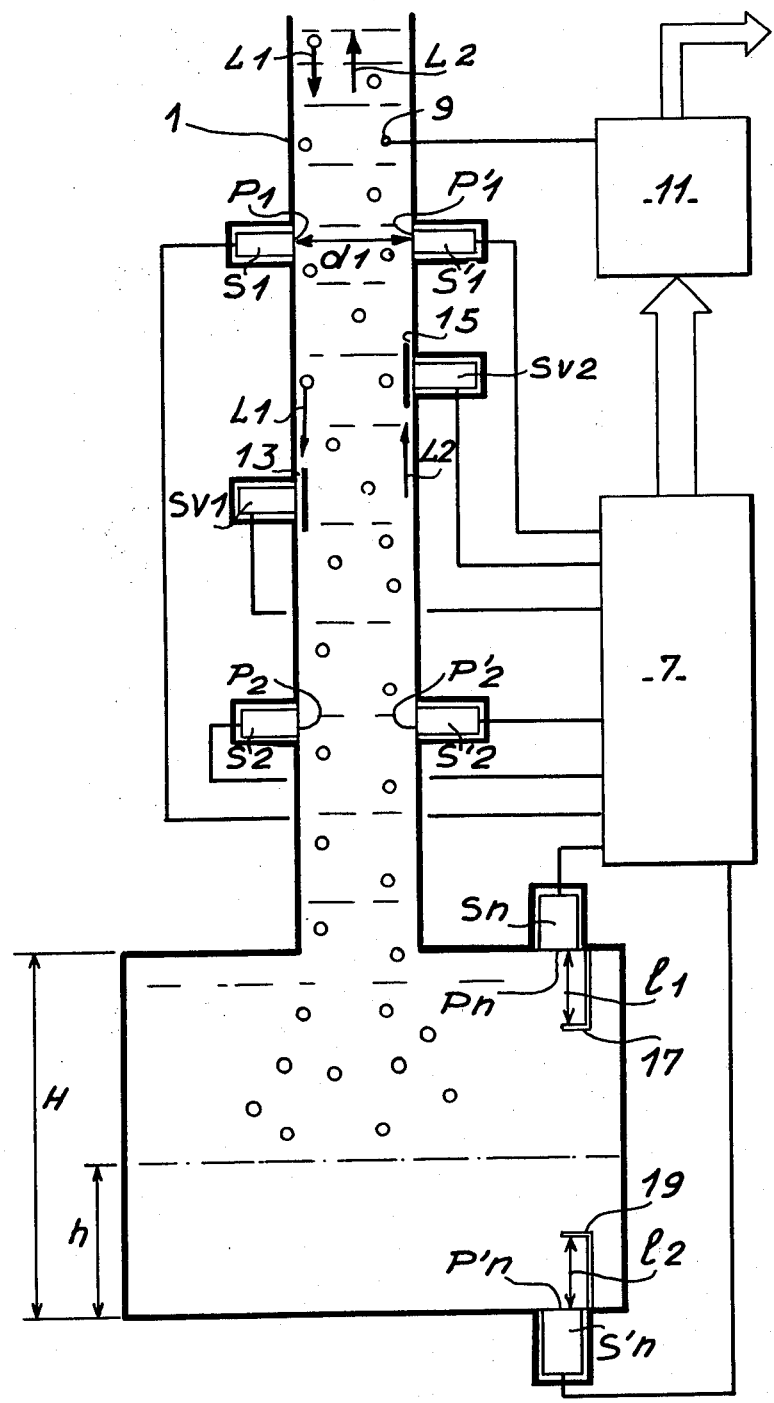

PROCESS AND DEVICE FOR MONITORING THE FUNCTIONING OF A LIQUID-LIQUID EXTRACTION COLUMN

The present invention relates to a process and a device for monitoring the functioning of a liquid-liquid extraction column.

More precisely, it relates to a process for determining a characteristic representative of the state of the liquids present in a liquid-liquid extraction column such as a pulsed column.

It is known that liquid-liquid extraction processes present considerable interest for separating, for example, by means of an organic solvent, certain elements present in an aqueous solution. These liquid-liquid extraction processes are generally carried out in columns where the two liquid phases are circulated in countercurrent, the heavy phase being injected at the top of the column and the light phase at the bottom of the column. By the contacting of these two phases, the element to be separated is divided between each of the phases according to the laws of chemical thermodynamics and, depending on the affinity of an element for one of the phases, this element may be extracted almost completely and separated from the other elements.

These extraction columns generally comprise a central shaft provided with plates where the exchange of the elements between the two liquid phases is effected and two zones of disengagement located respectively at each of the ends of the column. In the central shaft, one of the liquid phases is maintained in the state of dispersion in the other liquid phase which constitutes the continuous phase. In the zones of disengagement, a separation is obtained between the two liquid phases; in particular, one of these zones of disengagement is used as decanter for ensuring coalescence of the dispersed phase. When the column functions in continuous light phase, the decanter is located at the lower end of the column; when it functions in continuous heavy phase, the decanter is, on the contrary, located at the upper end of the column. To obtain a satisfactory functioning of the extraction columns, usual practice consists in maintaining constant the interphase level, i.e. the level of separation of the two liquid phases, in the decanter. Thus, to monitor the functioning of an extraction column, it is necessary to measure the level of the interphase in the decanter, frequently.

Another means generally used for following the functioning of a liquid-liquid extraction column is to determine the rate of retention $\epsilon$ of the dispersed phase, i.e. the percentage by volume of the dispersed phase contained in a volume v of the column. Thus, the rate of retention $\epsilon$ may be represented by the following formula:

$$\epsilon = V_d/V$$

in which $V_d$ represents the volume of the dispersed phase contained in a volume V of the column.

This parameter is extremely important as it determines the functioning of the columns. In fact, if the rate of retention is low the drops of dispersed phase will easily pass in the column, but the rate of flow of matter extracted from this dispersed phase will be low; if the rate of retention is high, the efficiency will be greater, but there will be a risk of locally attaining too great a coalescence of the drops, which may lead to a reversal of phases and to blocking of the column.

Thus, the correct functioning zone is located between these two limiting situations. Consequently, it is of considerable interest to know, at any instant and at different points of the extraction column, the values of the rate of retention of the dispersed phase in order to monitor the functioning of this column.

Up to the present time, the rate of retention of the dispersed phase has been measured either by methods requiring the taking of a sample of the two-phase mixture present in the column, or by conductimetric methods.

In the methods necessitating a sample of the two-phase mixture, an electric or pneumatic valve is used for taking a sample of the mixture, then this mixture is left to decant and the respective volumes of the two phases are measured, this making it possible to determine the rate of retention. This method presents two drawbacks: the sampling disturbs the functioning of the extraction column, which may have serious consequences when the column is at the limit of blocking; measurement can only be effected episodically and the frequency must even be relatively low if the above-mentioned drawback is to be avoided.

The methods of measuring by conductimetry are only applied in the case of one of the phases only being conducting. In this case, the conductivity of the two-phase mixture is determined, which enables the voluminal percentage of the dispersed phase to be assessed.

However, this method can only be applied when the continuous phase is conducting; moreover, if the continuous phase is too conducting, the dispersion of an insulating phase in the conducting phase modifies the conductivity of the two-phase mixture only very slightly, at retention rates close to those used in the liquid-liquid extraction columns. This is, for example, the case when the conducting phase is a 2 or 3 N nitric acid solution.

It is precisely an object of the present invention to provide a process for monitoring the functioning of a liquid-liquid extraction column which avoids the above-mentioned drawbacks.

According to the invention, the process for monitoring the functioning of a liquid-liquid extraction column in which two non-mixing liquids constituted respectively by a heavy liquid L1 and by a light liquid L2 circulate in countercurrent, consists in determining the time t taken by an ultrasonic signal to propagate in the column from a point P to a point P' located at a distance d from point P, in determining the speeds of propagation of this ultrasonic signal in a first liquid medium and in a second liquid medium of which the compositions correspond substantially and respectively to two different zones of the liquid medium present in the column between points P and P', and in calculating from this time t, the distance d and the speeds thus determined, a characteristic representative of the state of the liquids L1 and L2 present in the column between points P and P'.

According to a first embodiment of the process according to the invention, the characteristic representative of the state of the liquids L1 and L2 is the value of the rate of retention of the dispersed liquid phase.

According to this first embodiment, the speed $v_1$ of propagation of an ultrasonic signal in the liquid L1 and the speed $v_2$ of propagation of an ultrasonic signal in liquid L2 are determined, an ultrasonic signal is emitted at a point P of said column, the passage of said signal to a distance d from point P, is then detected, the time t taken by said ultrasonic signal to cover the distance d is determined and the voluminal fraction $\epsilon_1$ of the liquid L1 and/or the voluminal fraction $\epsilon_2$ of the liquid L2 is calculated from the formulae:

$$\epsilon_1 = \frac{v_1}{d} \cdot \frac{v_2 t - d}{v_2 - v_1} \text{ and } \epsilon_2 = \frac{v_2}{d} \cdot \frac{v_1 t - d}{v_1 - v_2}$$

According to the process of the invention, the time t that an ultrasonic signal takes to cover distance d is thus determined, which then enables the retention rate or the voluminal fraction of one of the phases present in the column to be calculated, provided that the respective speeds $v_1$ and $v_2$ of propagation of this ultrasonic signal in the liquids L1 and L2 are known.

In fact, it is known that the speed of propagation of an ultrasonic signal depends on the characteristics of the medium in which it propagates. For a liquid, the main characteristics are as follows:
viscosity,
temperature,
density, etc.

Thus, the time taken by the signal to cover distance d in the two-phase medium constituted by the two liquids L1 and L2 corresponds to the sum of the times taken by this ultrasonic signal to cover each of the liquid phases L1 and L2 successively encountered.

Thus, when the distance d between emitter and receiver probe, the speed $v_1$ of sound in the liquid L1, the speed $v_2$ of sound in liquid L2, and the time t taken by the ultrasonic signal to cover distance d, are known, the relations are as follows:

$$t = \frac{\epsilon_1 d}{v_1} + \frac{(1 - \epsilon_1)d}{v_2} \text{ or } t = \frac{\epsilon_2 d}{v_2} + \frac{(1 - \epsilon_2)d}{v_1}$$

in which $\epsilon_1$ and $\epsilon_2$ correspond respectively to the voluminal fractions of the liquid phases L1 and L2 of the two-phase mixture.

$\epsilon_1$ and $\epsilon_2$ which correspond respectively to:

$$\epsilon_1 = \frac{v_1}{d} \cdot \frac{v_2 t - d}{v_2 - v_1} \text{ and } \epsilon_2 = \frac{v_2}{d} \cdot \frac{v_1 t - d}{v_1 - v_2},$$

may thus be calculated.

According to the invention, the influence of the temperature on the speeds $v_1$ and $v_2$ is preferably taken into account to determine the voluminal fractions $\epsilon_1$ and $\epsilon_2$.

To this end, the variations of the speeds $v_1$ and $v_2$ may previously be determined as a function of the temperature, the temperature T of the two-phase mixture present in the column may be detected, and, for calculating the voluminal fractions $\epsilon_1$ and $\epsilon_2$, the values of the speeds $v_1$ and $v_2$ which correspond to the detected temperature may be used.

According to the invention, this prior determination of the speeds $v_1$ and $v_2$ as a function of the temperature is avoided by directly measuring in the column the respective speeds $v_1$ and $v_2$ of propagation of the ultrasonic signal in the liquid phases L1 and L2. Thus, the values of $v_1$ and $v_2$ which correspond to the temperature T of the mixture present in the column are directly obtained.

For directly measuring the speeds $v_1$ and $v_2$, two cylindrical measuring cells are disposed in the column near the walls thereof. Each cell is adapted to receive only one of the liquid phases present in the column, which may be obtained by appropriately choosing the material constituting each of the cells. Thus, to obtain a cell capable of receiving only an aqueous phase, this cell will be made of a hydrophilic material which may easily be wetted by the aqueous phases, for example made of metal. On the other hand, to obtain a cell adapted to receive an organic phase, a hydrophobic material will be used, capable of being wetted by this organic phase, for example a plastics material.

On one of the walls of the measuring cell is placed an ultrasonic probe which emits an ultrasonic signal then detects this ultrasonic signal after reflection on the other wall of the cell. Thus, the time taken by the ultrasonic signal to cover twice the width of the cell is determined and the speed of propagation $v_1$ or $v_2$ of this ultrasonic signal in the liquid phase L1 or L2 present in this measuring cell is deduced therefrom.

The process of the invention presents the particular advantage of ensuring, in the course of functioning of the column, a measurement of the rate of retention, at different spots of this column, without disturbing functioning thereof since there is no taking of samples nor device inside the column. In fact, the devices for emitting and receiving these ultrasonic signals do not need to be in contact with the liquids and may be disposed in housings made in the walls of the column.

According to a second embodiment of the process of the invention, the characteristic representative of the state of the liquids in the column is the level of the interphase in the decanter.

In this second embodiment of the process of the invention, an ultrasonic signal is emitted at a point Pn located in the decanter of said column, the passage of said ultrasonic signal is then detected at a point P'n also located in said decanter at a distance H from point Pn so that the points Pn and P'n are located on either side of the level of the interphase in said decanter, points Pn and P'n being, moreover, disposed so that an ultrasonic signal emitted at point Pn and covering the path PnP'n propagates only in liquid L2 then in liquid L1, both exempt of dispersed phase; the time $t_n$ taken by said signal to cover distance H is determined, the speed $v_1$ of propagation of said ultrasonic signal in the liquid L1 present in said decanter is determined, the speed $v_2$ of propagation of said ultrasonic signal in liquid L2 present in said decanter is determined, and the level of the interphase in said decanter is determined from the time $t_n$, the distance H and the speeds $v_1$ and $v_2$.

The points Pn and P'n are advantageously located respectively on two opposite walls of the decanter and the level h of the interphase with respect to the bottom of the decanter is calculated by using the following formula:

$$h = \frac{t_n - \frac{H}{v_2}}{\frac{1}{v_1} - \frac{1}{v_2}}$$

The invention also relates to a device for monitoring the functioning of a liquid-liquid extraction column.

This device is characterised in that it comprises means for emitting an ultrasonic signal at at least one of the points P1, P2 ... Pn of said column, means for detecting an ultrasonic signal at at least one of the points P'1, P'2 ... P'n of said column, said points P'1, P'2 ... P'n being located respectively at a distance $d_1, d_2 ... d_n$ from points P1, P2 . . . Pn, means for determining at least one of the times $t_1, t_2 \ldots t_n$ taken by said signals to cover distances $d_1, d_2 \ldots d_n$ respectively, and means for calculating a characteristic representative of the state of the liquids present in the column from at least one of the times $t_1, t_2 \ldots t_n$ and the or each corresponding distance $d_1, d_2 \ldots d_n$.

This device also advantageously comprises means for detecting the temperature T of the mixture of liquids circulating in the column, means for elaborating an analog signal, called first signal, representative of one of the times $t_1, t_2 \ldots t_n$, means for elaborating an analog signal, called second signal, representative of the temperature T, and means for elaborating from said first signal and said second signal, an analog signal, called third signal, representative of one of the characteristics of the mixture of liquids circulating in the column.

According to a preferred embodiment of the device of the invention, specially adapted for measuring the rate of retention of the dispersed phase, the device comprises means for directly measuring in the column the speed $v_1$ of propagation of an ulrasonic signal in the liquid L1 and the speed $v_2$ of propagation of an ultrasonic signal in the liquid L2.

These means for measuring the speed $v_1$ or $v_2$ advantageously comprise a cylindrical measuring cell disposed in the column, said measuring cell being adapted to have only one of said liquids L1 or L2 which circulates in the column passing therethrough, and means for emitting an ultrasonic signal in said cell and for detecting the ultrasonic signal reflected on the wall of said cell.

In this embodiment of the device of the invention, said device preferably also comprises means for elaborating an analog signal, called first signal, representative of one of the times $t_1, t_2 \ldots t_n$, means for elaborating an analog signal, called fourth signal, representative of the speed $v_1$ measured directly in the column, means for elaborating an analog signal, called fifth signal, representative of the speed $v_2$ measured directly in the column, and means for elaborating from said first signal, said fourth signal and said fifth signal, a sixth analog signal representative of the rate of retention of the dispersed phase present in the column.

According to a variant embodiment of the device of the invention, more particularly adapted to measuring the level of the interphase in the decanter of the column, the device comprises means for emitting and detecting an ultrasonic signal at a point Pn, means for emitting and detecting an ultrasonic signal at a point P'n, points Pn and P'n being located on two walls of the decanter of the column so that they are disposed on either side of the level of the interphase in the decanter and an ultrasonic signal emitted at point Pn and passing over the path PnP'n propagates only in liquid L2 then liquid L1, both exempt of dispersed phase, first reflection means for reflecting an ultrasonic signal emitted at point Pn and second means for reflection, reflecting an ultrasonic signal emitted at point P'n, means for determining the time $t_{v2}$ taken by the ultrasonic signal emitted at point Pn to cover twice the distance between the point Pn and the first reflection means, means for determining the time $t_{v1}$ taken by the ultrasonic signal emitted at point P'n to cover twice the distance between point P'n and the second reflection means, and means for determining the time $t_n$ taken by an ultrasonic signal to cover the distance between points Pn and P'n.

Thus, the speed $v_1$ of propagation of an ultrasonic signal in the liquid L1 and the speed $v_2$ of propagation of an ultrasonic signal in liquid L2 present in the decanter may thus be directly determined.

According to this variant, the device preferably comprises, in addition, means for elaborating an analog signal, called seventh signal, representative of the time $t_{v2}$, means for elaborating an analog signal, called eighth signal, representative of the time $t_{v1}$, means for elaborating an analog signal, called ninth signal, representative of the time $t_n$, and means for elaborating from said seventh, eighth and ninth signals a tenth analog signal representative of the level h of the interphase in said decanter.

The invention will be more readily understood on reading the following description with reference to the accompanying drawings, in which:

The single FIGURE schematically shows a device for carrying out the process of the invention.

Referring now to the drawing, it shows a column 1 constituted for example by a pulsed column of circular section, having a height of 6 m and a diameter of 100 mm, in which is maintained in the state of dispersion a two-phase mixture comprising a liquid phase L1 dispersed in a continuous liquid phase L2.

To monitor the rate of retention of the dispersed phase present in this column, at least two ultrasonic probes S1 and S'1 are associated therewith, which each comprise a capsule emitting and receiving ultrasounds. These probes are respectively disposed in housings made in the wall of the column at points P1 and P'1 which are diametrically opposite, in the same transverse plane.

Thus, the distance $d_1$ covered by the ultrasonic signal in the two-phase mixture corresponds to the diameter of the column, i.e. to 100 mm.

Although this example illustrates the use of two ultrasonic probes disposed on either side of the column, it will be specified that a single ultrasonic probe associated with an ultrasonic reflector disposed in the column may be used. In this case, the probe will act successively as an emitter of an ultrasonic signal, then as detector of the reflected ultrasonic signal, the distance $d_1$ covered by the ultrasonic signal corresponding in this case to twice the distance between the probe and the reflector.

The capsules of the probes S1 and S'1 are ceramic capsules which emit an ultrasonic signal when a voltage is applied thereto and which are capable of detecting an ultrasonic signal and of converting it into voltage.

It will be noted that the two probes S1 and S'1 are connected to an electronic clock 7 which is triggered at the moment when the emitter probe S1 produces an ultrasonic signal and which stops at the moment when the probe S'1 detects the passage of this ultrasonic signal.

Thus, the electronic clock 7 measures the time $t_2$ lapsing between the emission and reception of the ultrasonic signal, i.e. the time $t_1$ that this signal takes to cover the distance $d_1$, propagating successively in the continuous phase and the dispersed phase present in the column, this time $t_1$ being increased by the time taken by this signal to propagate likewise in the walls disposed in front of the capsules of the probes S1 and S'1.

The probes S1 and S'1 which are disposed in the central part of the column are more particularly intended for measuring the rate of retention of the dispersed phase. When it is desired to follow this rate of retention in different parts of the column, the device also comprises other pairs of probes of the same type, located at different levels, such as the pair of probes S2 and S'2 arranged to emit an ultrasonic signal at point P2 and to detect the ultrasonic signal at point P'2, these probes S2 and S'2 also being connected to the electronic clock 7.

In order to take into account the influence of the temperature for determining the rate of retention, the device also comprises a temperature detector 9, constituted for example by a resistor probe of the platinum type of which the precision is greater than 0.1° C., which is disposed inside the column 1, slightly above the level of the probes S1 and S'1.

Furthermore, the device comprises means 11 for calculating from the signals emitted on the one hand by the electronic clock 7 and on the other hand by the temperature detector 9, the value of the voluminal fraction $\epsilon_1$ of the liquid phase L1 or of the voluminal fraction $\epsilon_2$ of the liquid phase L2.

These calculating means are constituted for example by analog modules or by a calculator in which certain data, particularly those concerning the values of the speeds $v_1$ and $v_2$ as a function of the temperature, have been previously introduced.

However, to avoid the prior measurement of these data and their introduction into the calculator 11, the speeds $v_1$ and $v_2$ can be measured directly in the column, this making it possible to obtain the values of the speeds $v_1$ and $v_2$ at the temperature of the column, directly.

To this end, the device comprises two measuring cells 13 and 15 disposed along the walls of the column. The measuring cell 13 is made of a material wettable by the dispersed phase and consequently, the dispersed phase L1 in the pure state may be isolated in this cell. The measuring cell 15 is made of a material wettable by the continuous phase, and, in the same way, the continuous phase L2 in the pure state is isolated in this measuring cell 15. Ultrasonic probes Sv1 and Sv2 are disposed in the vicinity of the cells 13 and 15 and they are also connected to the electronic clock 7. In this way, the time lapsing between the emission by the probe Sv1 of an ultrasonic signal in the cell 13 and its detection by the probe Sv1 after reflection on the wall of the cell 13 may be determined, as well as the time which lapses between the emission of an ultrasonic signal by the probe Sv2 in the cell 15 and the detection of this ultrasonic signal by this same probe Sv2 after reflection on the wall of the cell 15.

These data which are representative of the speeds $v_1$ and $v_2$ of propagation of an ultrasonic signal in the liquids L1 and L2 are also introduced into the calculating device 11.

The FIGURE also shows the lower part of the column which acts in this case as decanter, since, as shown in the drawing, the continuous phase L2 is the light phase. This decanter is constituted by a cylindrical part of larger diameter than the diameter of the column and of total height H, and it is also provided with ultrasonic probes Sn and S'n disposed on two opposite walls of the decanter and capable of emitting and detecting an ultrasonic signal at points Pn and P'n. As may be seen in the FIGURE, the points Pn and P'n are located in a zone of the decanter where the liquid L2 does not contain any dispersed phase. Thus, an ultrasonic signal emitted at point Pn will successively encounter only pure liquid L2 then decanted liquid L1. The probes Sn and S'n are associated with reflection means constituted by a metal screen 17 or 19 designed to reflect the ultrasonic signals emitted respectively by probes Sn and S'n.

These probes Sn and S'n are also connected to the electronic clock 7.

When the column functions, two non-mixing liquids are circulated therein in counter-current, one of said liquids constituting the dispersed phase L1 and the other the continuous phase L2. Periodically, an ultrasonic signal is produced at point P1 by applying an appropriate voltage to the capsule of the probe S1, this triggering the electronic clock 7. When the capsule of the probe S'1 detects the passage of this ultrasonic signal, the electronic clock 7 stops; and the time $t_1$ taken by the ultrasonic signal to cover the distance $d_1$ is thus measured. The electronic clock 7 then emits an analog signal, called first signal, representative of the time $t_1$ and this first signal is sent into the calculator 11.

Similarly, the temperature detector 9 emits an analog signal, called second signal, representative of the temperature T of the two-phase mixture which circulates in the column and this second signal is also introduced into the calculator 11.

The data concerning the values of the speeds $v_1$ and $v_2$ at temperature T are also introduced into this calculator.

When a temperature detector 9 is used for measuring the temperature in the column, this is effected by previously introducing into this calculator the data concerning the variations of the speeds $v_1$ and $v_2$ as a function of the temperature. From these data, and from the first and second analog signals, the calculator 11 then emits a third analog signal representative of the rate of retention of the dispersed phase.

In the case of two measuring cells such as cells 13 and 15 being used for directly measuring in the column the value of the speeds $v_1$ and $v_2$ at operational temperature, these data are introduced into the calculator 11 from the electronic clock 7 which elaborates an analog signal, called fourth signal representative of the speed $v_1$, i.e. of the duration $tv1$ taken by the ultrasonic signal emitted by the probe Sv1 to propagate in the cell 13 over a distance equivalent to twice the width of this cell. Similarly, the clock 7 elaborates an analog signal, called fifth signal representative of the speed $v_2$ of propagation of an ultrasonic signal in the liquid phase L2.

In this case, the calculator 11 then emits from the first, fourth and fifth signals, a sixth analog signal representative of the rate of retention $\epsilon$ of the dispersed phase present in the liquid-liquid extraction column.

By way of example, this device for measuring the rate of retention of the dispersed phase has been tested in the case of a liquid-liquid extraction made between an aqueous 0.1 M nitric acid solution and a solution of 30% tributyl phosphate in dodecane, the aqueous nitric acid solution constituting the continuous phase L2 and the tributyl phosphate the dispersed phase L1. In this example, the two-phase mixture was maintained in the state of dispersion by a pulsation device of which the amplitude and frequency were adjusted so as to cover the useful zone of the retention rates ranging from 0 to 40%, and the measurements were carried out with an ultrasonic signal of frequency close to 1 Mhertz.

In the case of these tests, the probes emitting and receiving ultrasonic waves S1 and S'1 were disposed half way up the column, in receiving housings made in the walls of the column, so that the distance d between the capsules of the two probes was 116 mm.

Firstly, to standardize the calculating device 11, measurements were made of speed of propagation of an ultrasonic signal of frequency close to 1 megahertz by filling the column with pure phase L1 or pure phase L2 in order to determine the variations in the speeds $v_1$ and $v_2$ as a function of the temperature and to introduce these data into the calculating device 11.

In the case of the dispersed phase L1 (tributyl phosphate), the following results were obtained:

TABLE 1

| T (°C.) | $t_1$ (μs) | $v_1$ (m · s$^{-1}$) |
|---|---|---|
| 19.4 | 91.4 | 1269.1 |
| 27.4 | 94.8 | 1223.6 | and in the case of the continuous phase L2 (nitric acid), the following results were obtained:

TABLE 2

| T (°C.) | $t_1$ (μs) | $v_2$ (m · s$^{-1}$) |
|---|---|---|
| 18.6 | 78.2 | 1483.3 |
| 26.8 | 77.2 | 1502.5 |

It will be specified that, for calculating the speeds $v_1$ and $v_2$ and the voluminal fractions $\epsilon_1$ and $\epsilon_2$, account is taken of the fact that the time $t_1$ measured by the clock includes not only the propagation time t of the ultrasonic signal in the two-phase mixture, but also the propagation time of this signal in the walls disposed in front of the capsules of the probes S1 and S'1. Assuming that the wall is thick, it would be possible to introduce the propagation time of the signal through the wall in the processing member, which would allow it to be subtracted from the time measured. For the experiment described, the ceramic capsule was placed behind a stainless steel wall of 0.1 mm and it was not necessary to take into account the wall to determine the propagation time.

Thus, it is seen that, for the dispersed phase L1, the slope of the straight line $t_1 = f(T)$ is 0.425 μs/°C. and that, for the continuous phase L2, the slope of the straight line $t_1 = f(T)$ is 0.122 μs/°C.

Table 3 groups together the results obtained by determining in this way the rate of retention of the dispersed phase at various temperatures. By way of comparison, this Table also indicates the results obtained when the rate of retention is measured under the same conditions by the method of sampling which consists in taking a sample and in then subjecting it to a decantation and in determining the respective volumes of dispersed phase and of continuous phase.

It is seen from the results given in following Table 3 that the process of the invention makes it possible to obtain results which are equivalent to those obtained by the method of sampling, this demonstrating the reliability of the process of the invention.

TABLE 3

| T (°C.) | $t_1$ (μs) | Rate of retention (%) measured by: | |
| | | Process of the invention | Method of sampling |
|---|---|---|---|
| 17.6 | 79.3 | 7.9 | 9 |
| 17.9 | 79.7 | 11.3 | 11.5 |
| 18.3 | 81.1 | 22.6 | 22 |
| 18.3 | 79.2 | 11.5 | 10.5 |
| 18.4 | 80.2 | 15.5 | 14 |
| 24.8 | 78.8 | 8.3 | 10 |
| 18.3 | 79.8 | 12.8 | 13.2 |
| 18.1 | 83.4 | 40.8 | 38 |
| 18.1 | 79.7 | 11.4 | 12.7 |
| 18.1 | 79 | 5.9 | 5.5 |

Similarly, the process and the device of the invention make it possible to obtain very satisfactory results as far as the measurement of the level of the interphase in the decanter is concerned.

To make this measurement, the following operations are successively carried out. Firstly, the speed of propagation $v_2$ of an ultrasonic signal in the continuous phase L2 present in the decanter and the speed of propagation $v_1$ of an ultrasonic signal in the decanted liquid L1 are directly measured in the decanter. To this end, an ultrasonic signal is produced at point Pn by using the probe Sn and the electronic clock 7 is triggered at the moment of emission of this signal, then probe Sn is used for detecting the signal which reflected on the metal wall 17, this stopping the electronic clock 7. In this way, the time $t_{v2}$ taken by the ultrasonic signal to cover twice the distance $l_1$ between the probe Sn and the metal wall 17 is measured. The electronic clock 7 then emits an analog signal, called seventh signal representative of the time $t_{v2}$ and this seventh signal is sent in the calculator 11. Similarly, the speed $v_1$ of propagation of an ultrasonic signal in the decanted liquid L1 is determined by successively using the probe S'n as emitter then detector of the ultrasonic signal reflected on the wall 19. The electronic clock thus measures the time $t_{v1}$ taken by the ultrasonic signal to cover twice the distance $l_2$ between the probe S'n and the reflector 19 and it also emits an analog signal, called eighth signal representative of the time $t_{v1}$ and this signal is sent in the calculator 11.

After these two prior measurements, an ultrasonic signal is produced at point Pn, using the probe Sn as emitter probe and the ultrasonic signal is detected at point P'n using the probe S'n as detector probe, the electronic clock having been triggered upon emission of this signal and stopped upon detection of this signal at point P'n, his making it possible to measure the time $t_n$ taken by the ultrasonic signal to cover the distance between the points Pn and P'n which corresponds to the height of the decanter, or H. The electronic clock 7 then emits an analog signal called ninth signal representative of the time $t_n$, and this signal is sent in the calculator 11.

The calculator 11 determines from these three successive measurements the level h of the interphase from the following formula:

$$h = \frac{t_n - \frac{H}{v_2}}{\frac{1}{v_2} - \frac{1}{v_2}}$$

and it produces a tenth analog signal representative of the level h of the interphase in the decanter.

In this formula, $v_2$ is equal to $2l_1/t_{v2}$ and $v_1$ is equal to $2l_2/t_{v1}$.

It will be specified that the level h is defined with respect to the bottom of the decanter.

By way of examples, the results obtained concerning the measurement of the level of the interphase made in the decanter of a pulsed column provided with perforated plates in which an organic phase constituted by 30% tributyl phosphate in dodecane and an aqueous phase constituted by 3 N nitric acid, the organic phase constituting the continuous phase, are brought into contact in countercurrent, are given hereinafter. The characteristics of the device were as follows:

Column:
 Height: 6 m
 Diameter: 50 mm
Decanter:
 Diameter: 145 mm
 Height H: 250.1 mm
 Construction material: glass
Positioning of the probes Sn and S'n
 H: 250.1 mm
distance between the probe Sn and the reflector 17, $l_1$: 15.1 mm
 distance between the probe S'n and the reflector 19, $l_2$: 13 mm
Measurement and processing system:
 INTEL 80/30 Microprocessor (calculator 11.)

In this example, the interphase has been voluntarily measured at different levels. Table 4 hereinbelow gives the precision of the calculation with respect to the value measured directly with the aid of a triple decimeter ruler.

TABLE 4

| Level h: measured directly (mm) | Level h: calculated according to the invention (mm) | Deviation with respect to the direct measurement (%) |
| --- | --- | --- |
| 50 | 52 | 4 |
| 75 | 74 | 1.33 |
| 100 | 99 | 1 |
| 125 | 123 | 1.6 |
| 150 | 149 | 0.7 |
| 175 | 175 | 0 |
| 200 | 202 | 1 |

What is claimed is:

1. Process for monitoring the functioning of a liquid-liquid extraction column in which two non-mixing liquids, constituted respectively by a heavy liquid L1 and a light liquid L2, circulate in countercurrent, said process comprising the following steps of:
 determining the time t taken by an ultrasonic signal to propagate in the column from a point P to a point P' located at a distance d from point P,
 determining the speeds $v_1$ and $v_2$ of propagation of this ultrasonic signal in the liquid L1 and in the liquid L2 respectively, and
 calculating from this time t, the distance d and the speeds $v_1$ and $v_2$ thus determined, the voluminal fraction $\epsilon_1$ of the liquid L1 and/or the voluminal fraction $\epsilon_2$ of the liquid L2 from the formula:

$$\epsilon_1 = \frac{v_1}{d} \cdot \frac{v_2 t - d}{v_2 - v_1} \text{ and } \epsilon_2 = \frac{v_2}{d} \cdot \frac{v_1 t - d}{v_1 - v_2}.$$

2. The process of claim 1, which further comprises determining the variations of the speeds $v_1$ and $v_2$ as a function of the temperature, determining the temperature T of the two-phase mixture present in said column, and calculating the voluminal fraction $\epsilon_1$ and/or the voluminal fraction $\epsilon_2$ from the values of $v_1$ and $v_2$ which correspond to said temperature T.

3. The process of claim 1, wherein the speed $v_1$ of propagation of the ultrasonic signal in the liquid L1 and the speed $v_2$ of propagation of the ultrasonic signal in the liquid L2 are determined directly in the column.

4. Process for monitoring the functioning of a liquid-liquid extraction column in which two non mixing liquids, constituted respectively by a heavy liquid L1 and a light liquid L2, circulate in countercurrent, said process comprising the following steps of:
 determining the time $t_n$ taken by an ultrasonic signal to propagate in the column from a point $P\omega$ to a point P'n located in the decanter of said column, at a distance H from point Pn so that points Pn and P'n are located on either side of the level of the interphase in said decanter, and being disposed, in addition, so that an ultrasonic signal emitted at point Pn and passing over the path PnP'n propagates solely in liquid L2 then liquid L1, both exempt of dispersed phase,
 determining the speed $v_1$ of propagation of said ultrasonic signal in the liquid L1 present in said decanter and the speed $v_2$ of propagation of said ultrasonic signal in the liquid L2 present in said decanter,
 calculating the level of the interphase in said decanter from time $t_n$, the distance H and the speeds $v_1$ and $v_2$.

5. The process of claim 4, wherein the points Pn and P'n are respectively located on two opposite walls of the decanter and the level h of the interphase with respect to the bottom of the decanter is calculated by using the following formula:

$$h = \frac{t_n - \frac{H}{v_2}}{\frac{1}{v_1} - \frac{1}{v_2}}$$

6. Device for monitoring the functioning of a liquid-liquid extraction column, comprising: means for emitting an ultrasonic signal of at least one of points P1, P2 ... Pn of said column, means for detecting an ultrasonic signal of at least one of points P'1, P'2 ... P'n of said column, said points P'1, P'2 ... P'n being located respectively at a distance $d_1, d_2 ... d_n$ from points P1, P2 ... Pn, means for determining at least one of the times $t_1, t_2 ... t_n$ taken by said signals to cover distances $d_1, d_2 ... d_n$ respectively, and means for calculating a characteristic representative of the state of the liquids present in the column from at least one of the times $t_1, t_2 ... t_n$ and the or each of the corresponding distances $d_1, d_2 ... d_n$, this characteristic being selected among the voluminal fraction $\epsilon_1$ of the liquid L1, the voluminal fraction $\epsilon_2$ of the liquid L2 and the level of the interphase in the decanter of said column.

7. The device of claim 6, further comprising means for detecting the temperature T of the mixture of liquids circulating in said column, means for generating an analog signal, called first signal, representative of one of the times $t_1, t_2 ... t_n$, means for generating an analog signal, called second signal, representative of temperature T, and means for generating from said first signal and said second signal an analog signal, called third signal, representative of one of the characteristics of the mixture circulating in said column.

8. The device of claim 6, further comprising means for directly measuring, in the column, the speed $v_1$ of propagation of an ultrasonic signal in the liquid L1 and the speed $v_2$ of propagation of an ultrasonic signal in the liquid L2.

9. The device of claim 8, wherein said means for measuring the speed $v_1$ or $v_2$ comprise a cylindrical measuring cell disposed in the column, said measuring cell being adapted to have only one of the liquids L1 or L2 which circulate in the column, passing therethrough, and means for emitting an ultrasonic signal in said cell and for detecting the ultrasonic signal reflected on the wall of said cell.

10. The device of either one of claims 8 or 9 further comprising means for generating an analog signal, called first signal, representative of one of the times $t_1$, $t_2 \ldots t_n$, means for generating an analog signal, called fourth signal, representative of the speed $v_1$ measured directly in the column, means for generating an analog signal, called fifth signal, representative of the speed $v_2$ measured directly in the column, and means for generating from said first signal, said fourth signal and said fifth signal, a sixth analog signal representative of the rate of retention of the dispersed phase present in the column.

11. The device of claim 6, further comprising means for emitting and detecting an ultrasonic signal at a point Pn, means for emitting and detecting an ultrasonic signal at a point P'n, points Pn and P'n being located on two walls of the decanter of the column so that they are disposed on either side of the level of the interphase in the decanter and an ultrasonic signal emitted at point Pn and passing over the path PnP'n propagates solely in liquid L2 then liquid L1, both exempt of dispersed phase, first reflection means for reflecting an ultrasonic signal emitted at point Pn and second reflection means for reflecting an ultrasonic signal emitted at point P'n, means for determining the time $t_{v2}$ taken by the ultrasonic signal emitted at point Pn to cover twice the distance between point Pn and the first reflection means, means for determining the time $t_{v1}$ taken by the ultrasonic signal emitted at point P'n to cover twice the distance between point P'n and the second reflection means, and means for determining the time $t_n$ taken by an ultrasonic signal to cover the distance between points Pn and P'n.

12. The device of claim 11, further comprising means for generating an analog signal, called seventh signal, representative of the time $t_{v2}$, means for generating an analog signal, called eighth signal, representative of the time $t_{v1}$, means for generating an analog signal called ninth signal representative of the time $t_n$, and means for generating from said seventh, eighth and ninth signals a tenth analog signal representative of the level h of the interphase in said decanter.

* * * * *